United States Patent
Taneja et al.

(10) Patent No.: US 9,238,029 B2
(45) Date of Patent: *Jan. 19, 2016

(54) MULTIPLE PPI DOSAGE FORM

(71) Applicant: TAKEDA PHARMACEUTICALS U.S.A., INC., Deerfield, IL (US)

(72) Inventors: Rajneesh Taneja, Libertyville, IL (US); Majid Vakilynejad, Pleasant Prairie, WI (US)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 295 days.

This patent is subject to a terminal disclaimer.

(21) Appl. No.: 13/874,219

(22) Filed: Apr. 30, 2013

(65) Prior Publication Data

US 2013/0245071 A1 Sep. 19, 2013

Related U.S. Application Data

(63) Continuation of application No. 11/629,016, filed as application No. PCT/US2005/019028 on Jun. 1, 2005, now Pat. No. 8,461,187.

(60) Provisional application No. 60/580,265, filed on Jun. 16, 2004.

(51) Int. Cl.
*A61K 31/44* (2006.01)
*A61K 31/34* (2006.01)
*A61K 31/4439* (2006.01)
*A61K 9/00* (2006.01)

(52) U.S. Cl.
CPC ........... *A61K 31/4439* (2013.01); *A61K 9/0004* (2013.01)

(58) Field of Classification Search
CPC .................. A61K 31/4439; A61K 9/0004
USPC .......................................... 514/338; 424/469
See application file for complete search history.

(56) References Cited

U.S. PATENT DOCUMENTS

| | | | |
|---|---|---|---|
| 2,957,880 | A | 10/1960 | Romesh |
| 2,996,431 | A | 8/1961 | Barry |
| 4,182,756 | A | 1/1980 | Ramsay |
| 4,464,170 | A | 8/1984 | Clemens |
| 4,600,577 | A | 7/1986 | Didriksen |

(Continued)

FOREIGN PATENT DOCUMENTS

| | | |
|---|---|---|
| CA | 2383306 | 4/2001 |
| CA | 2536902 | 3/2005 |

(Continued)

OTHER PUBLICATIONS

Hirai, S. et al., "Formulation studies of an acid-unstable antiulcer drug, Lansoprazole," Pharm. Tech Japan (1992) 8 (2):89-95.

(Continued)

*Primary Examiner* — San-Ming Hui
(74) *Attorney, Agent, or Firm* — Lisa V. Mueller; Michael Best & Friedrich LLP

(57) ABSTRACT

Herein provided are dosage forms (variously referred to as "formulations") comprising a PPI that is released from the dosage form as a first and a second dose. Each dose of PPI is present in an amount sufficient to raise the plasma levels of the PPI to at least 100 ng/ml.

22 Claims, 1 Drawing Sheet

(56) References Cited

U.S. PATENT DOCUMENTS

| | | |
|---|---|---|
| 4,628,098 A | 12/1986 | Nohara et al. |
| 4,728,512 A | 3/1988 | Mehta |
| 4,773,907 A | 9/1988 | Urquhart |
| 4,777,049 A | 10/1988 | Magruder |
| 4,783,337 A | 11/1988 | Wong et al. |
| 4,786,505 A | 11/1988 | Lovgren et al. |
| 4,853,230 A | 8/1989 | Lovgren et al. |
| 4,863,742 A | 9/1989 | Panoz et al. |
| 4,871,549 A | 10/1989 | Ueda |
| 4,894,240 A | 1/1990 | Geoghegan et al. |
| 4,904,476 A | 2/1990 | Mehta et al. |
| 4,980,170 A | 12/1990 | Schneider et al. |
| 5,011,692 A | 4/1991 | Fujioka |
| 5,017,381 A | 5/1991 | Maruyama |
| 5,026,560 A | 6/1991 | Makino et al. |
| 5,045,321 A | 9/1991 | Makino et al. |
| 5,093,132 A | 3/1992 | Makino et al. |
| 5,133,974 A | 7/1992 | Paradissis et al. |
| 5,178,867 A | 1/1993 | Guittard et al. |
| 5,178,878 A | 1/1993 | Wehling et al. |
| 5,229,131 A | 7/1993 | Amidon et al. |
| 5,229,134 A | 7/1993 | Mention et al. |
| 5,260,068 A | 11/1993 | Chen |
| 5,260,069 A | 11/1993 | Chen |
| 5,264,223 A | 11/1993 | Yamamoto et al. |
| 5,330,982 A | 7/1994 | Tyers |
| 5,348,748 A | 9/1994 | Sheth et al. |
| 5,401,512 A | 3/1995 | Rhodes et al. |
| 5,431,917 A | 7/1995 | Yamamoto et al. |
| 5,433,959 A | 7/1995 | Makino et al. |
| 5,445,829 A | 8/1995 | Paradissis et al. |
| 5,476,669 A | 12/1995 | Borody |
| 5,516,351 A | 5/1996 | Solomon et al. |
| 5,578,732 A | 11/1996 | Kato et al. |
| 5,582,837 A | 12/1996 | Shell |
| 5,631,020 A | 5/1997 | Okada et al. |
| 5,631,021 A | 5/1997 | Okada et al. |
| 5,639,476 A | 6/1997 | Oshlack et al. |
| 5,639,478 A | 6/1997 | Makino et al. |
| 5,643,607 A | 7/1997 | Okada et al. |
| 5,652,146 A | 7/1997 | Kell |
| 5,656,290 A | 8/1997 | Kelm et al. |
| 5,716,640 A | 2/1998 | Kamei et al. |
| 5,726,316 A | 3/1998 | Crooks et al. |
| 5,753,265 A | 5/1998 | Bergstrand et al. |
| 5,763,396 A | 6/1998 | Weiner et al. |
| 5,807,577 A | 9/1998 | Ouali |
| 5,814,342 A | 9/1998 | Okada et al. |
| 5,817,338 A | 10/1998 | Bergstrand et al. |
| 5,834,024 A | 11/1998 | Heinicke et al. |
| 5,837,284 A | 11/1998 | Mehta et al. |
| 5,879,708 A | 3/1999 | Makino et al. |
| 5,889,051 A | 3/1999 | Chen et al. |
| 5,900,252 A | 5/1999 | Calanchi et al. |
| 5,945,124 A | 8/1999 | Sachs et al. |
| 5,948,789 A | 9/1999 | Larsson et al. |
| 6,036,976 A | 3/2000 | Takechi et al. |
| 6,096,339 A | 8/2000 | Ayer et al. |
| 6,110,494 A | 8/2000 | Clancy et al. |
| 6,126,969 A | 10/2000 | Shah et al. |
| 6,162,463 A | 12/2000 | Lippa |
| 6,228,398 B1 | 5/2001 | Devane et al. |
| 6,274,173 B1 | 8/2001 | Sachs et al. |
| 6,328,994 B1 | 12/2001 | Shimizu et al. |
| 6,369,085 B1 | 4/2002 | Cotton et al. |
| 6,462,058 B1 | 10/2002 | Fujishima et al. |
| 6,605,303 B1 | 8/2003 | Karehill et al. |
| 6,610,323 B1 | 8/2003 | Lundberg et al. |
| 6,627,223 B2 | 9/2003 | Percel et al. |
| 6,635,276 B1 | 10/2003 | Von Falkenhausen |
| 6,635,280 B2 | 10/2003 | Shell et al. |
| 6,664,276 B2 | 12/2003 | Fujishima et al. |
| 6,780,436 B1 | 8/2004 | Lopez-Cabrera et al. |
| 6,897,205 B2 | 5/2005 | Beckert et al. |
| 6,939,971 B2 | 9/2005 | Fujishima et al. |
| 6,982,275 B2 | 1/2006 | Hashimoto et al. |
| 7,147,869 B2 | 12/2006 | Dietrich et al. |
| 7,169,799 B2 | 1/2007 | Hashimoto et al. |
| 7,271,182 B2 | 9/2007 | Kamiyama et al. |
| 7,285,668 B2 | 10/2007 | Hashimoto et al. |
| 7,339,064 B2 | 3/2008 | Fujishima et al. |
| 7,569,697 B2 | 8/2009 | Fujishima et al. |
| 7,737,282 B2 | 6/2010 | Fujishima et al. |
| 7,790,755 B2 | 9/2010 | Akiyama et al. |
| 8,030,333 B2 | 10/2011 | Fujishima et al. |
| 8,173,158 B2 | 5/2012 | Lee et al. |
| 2001/0008900 A1 | 7/2001 | Cederberg et al. |
| 2002/0034541 A1 | 3/2002 | Valducci |
| 2002/0042433 A1 | 4/2002 | Yelle et al. |
| 2002/0044962 A1 | 4/2002 | Cherukuri et al. |
| 2003/0008903 A1 | 1/2003 | Barberich et al. |
| 2003/0091630 A1 | 5/2003 | Louie-Helm et al. |
| 2003/0152627 A1 | 8/2003 | Beckert et al. |
| 2003/0153766 A1 | 8/2003 | Hashimoto et al. |
| 2003/0171591 A1 | 9/2003 | Hashimoto et al. |
| 2003/0180352 A1 | 9/2003 | Patel et al. |
| 2003/0181487 A1 | 9/2003 | Kamiyama et al. |
| 2004/0049045 A1 | 3/2004 | Hashimoto et al. |
| 2004/0146558 A1 | 7/2004 | Hirata et al. |
| 2004/0265370 A1 | 12/2004 | Odidi et al. |
| 2005/0003005 A1 | 1/2005 | Shimizu et al. |
| 2005/0147663 A1 | 7/2005 | Mohan et al. |
| 2005/0226929 A1 | 10/2005 | Xie et al. |
| 2005/0228026 A1 | 10/2005 | Fujishima et al. |
| 2006/0018964 A1 | 1/2006 | Combessis et al. |
| 2006/0024362 A1 | 2/2006 | Seth |
| 2006/0057195 A1 | 3/2006 | Nonomura et al. |
| 2006/0159760 A1 | 7/2006 | Yoneyama |
| 2006/0257467 A1 | 11/2006 | Kostadinov et al. |
| 2007/0026071 A1 | 2/2007 | Namburi et al. |
| 2007/0042033 A1 | 2/2007 | Venkata Ramana Rao |
| 2007/0141137 A1 | 6/2007 | Nagahara |
| 2008/0193522 A1 | 8/2008 | Meier et al. |
| 2008/0193540 A1 | 8/2008 | Soula et al. |
| 2008/0200482 A1 | 8/2008 | Petereit et al. |
| 2009/0098199 A1 | 4/2009 | Lee et al. |
| 2009/0215830 A1 | 8/2009 | Taneja |
| 2009/0220611 A1 | 9/2009 | Dargelas et al. |
| 2009/0263475 A1 | 10/2009 | Manne et al. |
| 2010/0068921 A1 | 3/2010 | Richter |
| 2010/0272798 A1 | 10/2010 | Akiyama et al. |
| 2010/0278911 A1 | 11/2010 | Akiyama et al. |
| 2010/0285120 A1 | 11/2010 | Akiyama et al. |
| 2011/0159088 A1 | 6/2011 | Guimberteau et al. |
| 2011/0189271 A1 | 8/2011 | Lad et al. |
| 2011/0223244 A1 | 9/2011 | Liversidge et al. |
| 2011/0274752 A1 | 11/2011 | Cifter et al. |
| 2011/0274753 A1 | 11/2011 | Cifter et al. |
| 2011/0274754 A1 | 11/2011 | Cifter et al. |

FOREIGN PATENT DOCUMENTS

| | | |
|---|---|---|
| CA | 2557791 | 10/2005 |
| CA | 2634637 | 7/2007 |
| DE | 4035455 | 11/1990 |
| EP | 0274734 | 7/1988 |
| EP | 0694547 | 1/1996 |
| EP | 0924519 | 6/1999 |
| EP | 0960620 | 12/1999 |
| EP | 1044682 | 10/2000 |
| EP | 1607088 | 12/2005 |
| EP | 1728512 | 12/2006 |
| JP | 59-227817 | 12/1984 |
| JP | 60-228410 | 11/1985 |
| JP | 2552937 | 12/1991 |
| JP | 2000355540 | 12/2000 |
| JP | 2001122769 | 5/2001 |
| JP | 2002501895 | 1/2002 |
| WO | 91/07172 | 5/1991 |
| WO | WO 93/18755 | 9/1993 |
| WO | 95/01783 | 1/1995 |
| WO | WO 96/01623 | 1/1996 |
| WO | WO 96/02535 | 2/1996 |
| WO | WO 96/17077 | 6/1996 |

(56) References Cited

FOREIGN PATENT DOCUMENTS

| | | |
|---|---|---|
| WO | WO 96/24338 | 8/1996 |
| WO | WO 97/02020 | 1/1997 |
| WO | WO 97/02261 | 1/1997 |
| WO | WO 97/25064 | 7/1997 |
| WO | WO 97/32573 | 9/1997 |
| WO | WO 94/48380 | 12/1997 |
| WO | WO 97/48380 | 12/1997 |
| WO | WO 98/21201 | 5/1998 |
| WO | WO 98/22118 | 5/1998 |
| WO | 98/29095 | 7/1998 |
| WO | WO 98/28294 | 7/1998 |
| WO | WO 99/03453 | 1/1999 |
| WO | WO 99/26698 | 6/1999 |
| WO | WO 99/32091 | 7/1999 |
| WO | WO 99/32093 | 7/1999 |
| WO | WO 99/38511 | 8/1999 |
| WO | WO 99/38512 | 8/1999 |
| WO | WO 99/38513 | 8/1999 |
| WO | WO 99/51203 | 10/1999 |
| WO | WO 99/58107 | 11/1999 |
| WO | WO 00/09092 | 2/2000 |
| WO | WO 00/25752 | 5/2000 |
| WO | 01/24777 | 4/2001 |
| WO | WO 01/37808 | 5/2001 |
| WO | 01/89483 | 11/2001 |
| WO | WO 02/39980 | 5/2002 |
| WO | WO 02/060415 | 8/2002 |
| WO | WO 03/086366 | 10/2003 |
| WO | WO 2004/035020 | 4/2004 |
| WO | WO 2004/035052 | 4/2004 |
| WO | 2004/038428 | 5/2004 |
| WO | WO 2004/045580 | 6/2004 |
| WO | 2004/058275 | 7/2004 |
| WO | 2004/082665 | 9/2004 |
| WO | 2004/093875 | 11/2004 |
| WO | 2006/009602 | 1/2006 |
| WO | WO 2006/044202 | 4/2006 |
| WO | WO 2006/056712 | 6/2006 |
| WO | WO 2006/122925 | 11/2006 |
| WO | WO 2006/125483 | 11/2006 |
| WO | WO 2007/006353 | 1/2007 |
| WO | WO 2007/036671 | 4/2007 |

OTHER PUBLICATIONS

Hunt, R.H., "Review article: the unmet needs in delayed-release proton-pump inhibitor therapy in 2005" Aliment Pharmacol. Ther. (2005) 22(Suppl 3):10-19.

Katz, P.O. et al., "Review article: acid-related disease—what are the unmet clinical needs?" Aliment Pharmacol. Ther. (2006) 23(Suppl 2):9-22.

Lee, R.D. et al., "The effect and timing of food on the pharmacokinetics and pharmacodynamics of TAK-390MR (modified release): evidence for dosing flexibility," Abstracts (2007) S145.

Munaza, A. et al., "Patterns of proton pump inhibitor use in inflammatory bowel disease (IBD) and concomitant risk of Clostridium difficile infection," Gastroenterology (2007) 132(4):A513—Digestive Disease Week Meeting/108th Annual Meeting of the American-Gastroenterological-Association; Washington, DC, May 19-24, 2007 Meeting Abstract.

Scarpignato, C. et al., "Acid suppression therapy: where do we go from here?" Digestive Diseases (2006) 24:11-46.

Sostek, M.B. et al., "Effect of timing of dosing in relation to food intake on the pharmacokinetics of esomeprazole," Br. J. Clin. Pharm. (2007) 64(3):386-390.

Zhang, W. et al., "Pharmacokinetic (PK), pharmacodynamic (PD), and safety evaluation of single and multiple 60 Mg, 90Mg, and 120Mg oral doses of modified release tak-390 (Tak-390mr) and 30 MG oral doses of lansoprazole (Lan) in healthy subjects," Gastroenterology (2007) 4(Suppl. 2):A487—Digestive Disease Week Meeting/108th Annual Meeting of the American-Gastroenterological-Association; Washington, DC, May 19-24, 2007, Meeting Abstract.

Office Action for U.S. Appl. No. 11/629,016 dated Mar. 17, 2010 (9 pages).

Office Action for U.S. Appl. No. 11/629,016 dated Nov. 23, 2010 (11 pages).

Office Action for U.S. Appl. No. 11/629,016 dated Mar. 28, 2012.

Office Action for U.S. Appl. No. 12/249,258 dated Apr. 12, 2011.

Notice of Allowance for U.S. Appl. No. 11/629,016 dated May 6, 2013.

Notice of Allowance for U.S. Appl. No. 11/629,016 dated Apr. 10, 2013.

Notice of Allowance for U.S. Appl. No. 11/629,016 dated Sep. 12, 2012.

Notice of Allowance for U.S. Appl. No. 12/249,258 dated Jan. 13, 2013.

Abel, C. et al., "Dexlansoprazole in the treatment of esophagitis and gastroesophagael reflux disease," The Annals fo Pharmacotherapy, (2010) 44:871-877.

Arimori et al., "Pharmacokinetic differences between Lansoprazole enantiomers in rats," J. Pharma. Pharmacology (1998) 50:1241-1254.

Atwood, J.L. et al., "Hydrogen-bonded molecular capsules are stable in polar media," Chem. Commun. (2001) 2736-2377.

Balvanera, A. et al., "A normal coronary arteriogram in a very young man with Prinzmetal's variant angina: case report with review of the literature," Cardiovas. Dis. Bulletin of the Texas Heart Institute (1981) 8(4):537-545.

Barradell et al., "Lansoprazole: A review of its pharmacodynamic and pharmacokinetic properties and its therapeutic efficacy in acid-related disorders," Drugs (1992) 44(2):225-250.

Borner, K. et al., "Separation of lansoprazole enantiomers in human serum by HPLC," Chromat. (1998) 47(3-4):171-175.

Bowler, I.M. et al., "A double blind lipase for lipase comparison of a high lipase and standard pancreatic enzyme preparation in cystic fibrosis," Arch. Dis. In Childhood (1993) 68:227-230.

Brittain, H.G., "Methods for the characterization of polymorphs and solvates," in Polymorphism in Pharmaceutical Solids, Marcel Dekker Inc., New York (1999) Chapter 6, 227-278.

Concise Encyclopedia," Polymorphism" Jakubke et al. editors (1993) 872-873.

Cronlein, K. et al., "Characterization of delayed release lansoprazole multiparticulates: impact of biorelevant dissolution media," 5th World Meeting on Pharmaceutics (2006), poster reprint.

Efron, D. et al., "Side effects of methylphenidate and dexamphetamine in children with attention deficit hyperactiviy disorder: a double-blind, crossover trial," Pediatrics (1997) 100:662-666.

Figulla, H.R. et al., "Diltiazem improves cardiac function and exercise capacity in pateitns with idiopathic dilated cardiomyopathy: results of the diltiazem in dilated cardiomyopathy trial," Circ. (1996) 94(3):346-352.

Gerkensmeier, T. et al., "Self-assembly of 2,8,14,20-tetraisobutyl-5,11,17,23-tetrahydroxyresorc[4]arene," Eur. J. Org. Chem. (1999) 2257-2262.

Gordon, A.J. et al., The Chemist's Companion, A Handbook of Practica Data, Techniques, and References, John Wiley & Sons, New York (1972) 440-445.

Gottdiener, J.S. et al., "Effect of single-drug therapy on reduction of left atrial size in mild to moderate hypertension: comparison of six antihypertensive agents," Circulation (1998) 98:140-148.

Haleblian, J. et al., "Pharmaceutical applications of polymorphism," J. Pharm. Sci. (1969) 58(8):911-929.

Handbook of Pharmaceutical Excipients, Cellulose Acetate Phthalate, 4th Edition, R.C. Rowe et al., editors, Pharmaceutical Press, London (2003) 120-124; 301-305; 462-468; 538-540.

Hirschowitz, B.I. et al., "Long-term treatment with lansoprazole for patients with Zollinger-Ellison syndrome," Aliment Pharmacol. Ther. (1996) 10:507-522.

International Search Report and Written Opinion for Application No. PCT/US08/79520 dated Dec. 23, 2008.

International Search Report and Written Opinion for Application No. PCT/US2005/019028 dated Jun. 13, 2006.

(56) References Cited

OTHER PUBLICATIONS

Katsuki et al., "Determination of R(+)- and S(−)-Lansoprazole using chiral stationary-phase liquid chromatography and their enantioselective pharmacokinetics in humans," Pharm. Res. (1996) 13(4):611-615.
Kotar, B. et al., "Study of polymorphism of a novel antiulcer drug," Poster Session P3: Tuesday Sep. 17, 1996, S182.
Lee, R.D. et al., "Clinical trial: the effect and timing of food on the pharmacokinetics and pharmacodynamics of dexlansoprazole MR, a novel duel delayed released formulation of a proton pump inhibitor—evidence for dosing flexibility," Alimentary Pharmacology & Therapeutics (2009) 29:824-833.
Lin, A.Y. et al., "Study of crystallization of endogenous surfactant in eudragit NE30D-free films and its influence on drug-release properties of controlled-release diphenhydramine HCl pellets coated with eudragit NE30D," AAPS Pharmsci. (2001) 3:1-12.
Marvola, M. et al., "Enteric polymers as binders and coating materials in multiple-unit site-specific drug delivery systems," Eur. J. Pharm. Sci. (1999) 7:259-267.
Metz, D.C. et al., "Review article: dual delayed release formulation of dexlansoprazole MR, a novel approach to overcome the limitations of conventional single release proton pump inhibitor therapy," Alimentary Pharmacology & Therapeutics (2009) 29:928-937.
Mikawa, K. et al., "Lansoprazole reduces preoperative gastric fluid acidity and volume in children," Can. J. Anaesth. (1995) 42(6):467-472.
Nagaya et al., "Effects of the enantiomers of lansoprazole (Ag—1749) on H++K+)-ATPase activity in canine gastric microsomes and acid formation in isolated canine parietal cells," Biochem. Pharm. (1991) 42(10):1875-1878.
Ogura, T. et al., "HPMC Capsules—an alternative to gelatin," Pharm. Technology Europe (1998) 10(11):32-42.
Physician's Desk Reference, "Lansoprazole" (1997) 5 pages.
Physician's Desk Reference, "Prevacid," 55th Edition, Medical Economics Company, Inc., New Jersey (2001) 6 pages.
Remington: the Science and Practice of Pharmacy, 20th Edition, A.R. Gennaro, Editor (2000) 897 and 903.
Robinson, M. et al., "Effective maintenance treatment of reflux esophagitis with low-dose lansoprazole. A randomized, double-blind, placebo-controlled trial," Annals of Int. Med. (1996) 124(10):859-867.
Rouhi, A.M., "Concentrates and the right stuff. From research and development to the clinic, getting drug crystals right is full of pitfalls," Chem. Engineering News (2003) 31-35.
Sakamoto, T. et al., "Prolonged action preparation of cefaclor," Jap J. Antibiotics (1985) 38(3):813-821.
Sharma, V.K. et al., "Oral pharmacokinetics of omeprazole and lansoprazole after single and repeated doses as intact capsules or as suspensions in sodium bicarbonate," Aliment Pharmacol. Ther. (2000) 14:887-892.
Singh, B.N., "Modified-release solid formulations for colonic delivery," Recent Patents on Drug Delivery & Formations (2007) 1:53-65.
Srinivas, N.R. et al., "Enantioselective pharmacokinetics of dl-threo-methylphenidate in humans," Pharm. Res. (1993) 10(1):14-21.
Tietze et al., "Isolation and purification of reaction products," Chapter 1.5 of Reactions and Syntheses in the Organic Chemistry Laboratory (1989) 23-26.
United States Pharmacopeia, "Lansoprazole" the National Formulary USP 32, NF 27 (2009) 2:2751-2754.
United States Pharmacopeia, "X-ray diffraction," The National Formulary USP 25 NF 20 (2002) 2088-2089.
United States Pharmacopeia, "X-ray diffraction," The National Formulary USP23 NF 18 (1995) 1843-1844.
United States Pharmacopeia, "X-ray diffraction," The National Formulary USP28 NF 23 (2005) 2513-2514.
Vrecer, F. et al., "Study of influence of temperature and grinding on the crystalline state of lansoprazole," Chemical Abstract No. 127:362535h (1997) 127(1-2).
Vrecer, F. et al., "Study of influence of temperature and grinding on the crystalline state of lansoprazole," Farm. Vestn (1997) 242-243.
Wilkins, C.E. et al., "HIV—associated myocarditis treated with zidovudine (AZT)," Tex. Heart Inst. J. (1989) 16:44-45.
Yukawa, E., "Optimisation of antiepileptic drug therapy," Clin. Pharmacokinet. (1996) 31(2):120-130.
Bauer, F. et al. eds., Pharmazeutische Technologie, Auflage, Stuttgart, Chapter 14 (1997) 5:331-332.
Brogmann, B. et al., "Enteric targeting through enteric coating," Drug Targeting Technology, Schreier, H., editor, Marcel Dekker, New York, (2001) 1-49.
Fell, J.T., "Targeting of drugs and delivery systems to specific sites in the gastrointestinal tract," J. Anat. (1996) 189:517-519.
Huber, R. et al., "Review article: the continuing development of proton pump inhibitors with particular reference to pantoprazole," Aliment Pharmacol. Ther. (1995) 9:363-378.
Khan, M.Z.I. et al., "A pH-dependent colon targeted oral drug delivery system using methacrylic acid copolymers. I. Maipulation of drug release using Eudragit L100-55 and Eudragit S100 combinations," J. Control. Re. (1999) 58:215-222.
Tarcha, P.J., editor, Polymers for Enteric Coating Applications, Agyilirah, G.A. et al., Chapter 3 (1990) 39-66.
Vanderhoff, B.T. et al., "Proton pump inhibitors: an update," American Family Physician (2002) 66(2):273-280.
Wilding, I.R. et al.,, "Targeting of drugs and vaccines to the gut," Pharmac. Ther. (1994) 62:97-124.
Wittbrodt et al., "Delayed release dexlansoprazole in the treatment of GERD and erosive esophagitis," Clin. Exp. Gastroent. (2009) 2:117-128.
Notice of Opposition by Sanovel Ilac San. Ve Tic. A.S., dated Oct. 10, 2014 Against European Patent No. 1553929.
Declaration Under 37 CFR 1.132 by Takashi Kurasawa dated Dec. 4, 2009 (In Re Akiyama et al.).
Affidavit of Takashi Kurasawa, Nov. 30, 2009, In the Matter of Patent No. 223061 by Takeda Pharmaceuticals Co., Opposed by Dr. Reddy.
Main Request, dated Oct. 10, 2014.
Main Request—Clean, dated Oct. 10, 2014.
First Auxiliary Request, dated Oct. 10, 2014.
First Auxiliary Request—Clean, dated Oct. 10, 2014.
Second Auxiliary Request, dated Oct. 10, 2014.
Second Auxiliary Request—Clean, dated Oct. 10, 2014.
Third Auxiliary Request, dated Oct. 10, 2014.
Third Auxiliary Request—Clean, dated Oct. 10, 2014.
Fourth Auxiliary Request, dated Oct. 10, 2014.
Fourth Auxiliary Request—Clean, dated Oct. 10, 2014.
Fifth Auxiliary Request, dated Oct. 10, 2014.
Fifth Auxiliary Request—Clean, dated Oct. 10, 2014.
Acknowledgment of Receipt from the European Patent Office for Notice of Opposition for Application No. EP037541166 (Patent No. EP1553929), dated Oct. 10, 2014.
European Patent Office Action for Application No. 05754809.1 dated Mar. 6, 2015 (6 pages).
Avdeef, A., Absorption and Drug Development. Solubility, Permeability, and Charge State, John Wiley & Sons, NY (2003) p. 11-17.
Dressman, J.B. et al., "Upper gastrointestinal (GI) pH in young, health men and women," Pharm. Res. (1990) 7(7):756-761.
Fallingborg, J. et al., "pH-profile and regional transit times of the normal gut measured by a radiotelemetry device," Aliment. Pharmacol. Therap. (1989) 3:605-613.
Fallingborg, J., "Intraluminal pH of the human gastrointestinal tract," Danish Medical Bulletin (1999) 46(3):183-196.
Notari, R.E. Biopharmaceutics and Clinical Pharmacokinetics, Third Edition, Marcel Dekker, Inc., Chapter 4, entitled "Biopharmaceutics: clinical applications of pharmacokinetic parameters" (1980) 107-172.
Qui, Y. et al., Handbook of Pharmaceutical Controlled Release Technology, Marcel Dekker Inc., Chapter 23, "Research and Development Aspects of Oral Controlled-Release Dosage Forms," (2000) 465-503.
United States Department of Health and Human Services, "Guidance for industry food-effect bioavailability and federal bioequivalence studies," brochure (Dec. 2002).
Complaint for Patent Infringement in U.S. District Court, Northern District of California, Case No. CV-13/4001, *Takeda Pharmaceutical Co., Inc. et al.*, v. *Mylan Inc. et al.*, filed Aug. 28, 2013 (44 pages).

(56) References Cited

OTHER PUBLICATIONS

Defendants Mylan Inc.'s and Mylan Pharmaceuticals Inc.'s Answer to Plaintiffs' Complaint, Affirmative Defenses, and Counterclaims in the U.S. District Court, Northern District of California, Case No. CV-13/4001, *Takeda Pharmaceutical Co., Inc. et al.* v. *Mylan Inc. et al.*, filed Sep. 26, 2013 (29 pages).

Complaint for Declaratory Judgment, in the U.S. District Court, Northern District of California, *PAR Pharmaceutical, Inc. et al.*, vs. Takeda *Pharmaceutical Co., Ltd. et al.*, Case No. 5:13-CV-1927-LHK, filed Apr. 26, 2013 (7 pages).

First Amended Complaint for Patent Infringement, in the U.S. District Court, Northern District of California, *PAR Pharmaceutical, Inc. et al.*, vs. *Takeda Pharmaceutical Co., Ltd. et al.*, Case No. 5:13-CV-1927-LHK, filed Jul. 9, 2013 (10 pages).

Plaintiffs and Counterdefendants Par Pharmaceutical, Inc. and Handa Pharmaceuticals, LLC's First Amended Answer and Counterclaims to Defendant's and Counterclaims to Defendant's and Counterclaimants' First Amended Counterclaims in the U.S. District Court, Northern District of California, *PAR Pharmaceutical, Inc. et al.*, vs. *Takeda Pharmaceutical Co.*, Ltd. et al., Case No. 5:13-CV-1927-LHK, filed Aug. 16, 2013 (18 pages).

Defendant Impax Laboratories, Inc.'s Answer and Counterclaims to Plaintiffs Amended Complaint in the U.S. District Court, Northern District of California, *PAR Pharmaceutical, Inc. et al.*, vs. *Takeda Pharmaceutical Co., Ltd. et al.*, Case No. 5:13-CV-1927-LHK, filed Aug. 26, 2013 (13 pages).

Takeda's Answer to Plaintiffs and Counterdefendants PAR Pharmaceutical, Inc. and Handa Pharmaceuticals, LLC's Counterclaims to Defendants and Counterclaimants' First Amended Counterclaims in the U.S. District Court, Northern District of California, *PAR Pharmaceutical, Inc. et al.*, vs. *Takeda Pharmaceutical Co., Ltd. et al.*, Case No. 5:13- CV-1927-LHK, filed Sep. 6, 2013 (12 pages).

Second Amended Complaint for Patent Infringement in the U.S. District Court, Northern District of California, *PAR Pharmaceutical, Inc. et al.*, vs. *Takeda Pharmaceutical Co., Ltd. et al.*, Case No. 5:13-CV-1927-LHK, filed Oct. 29, 2013 (10 pages).

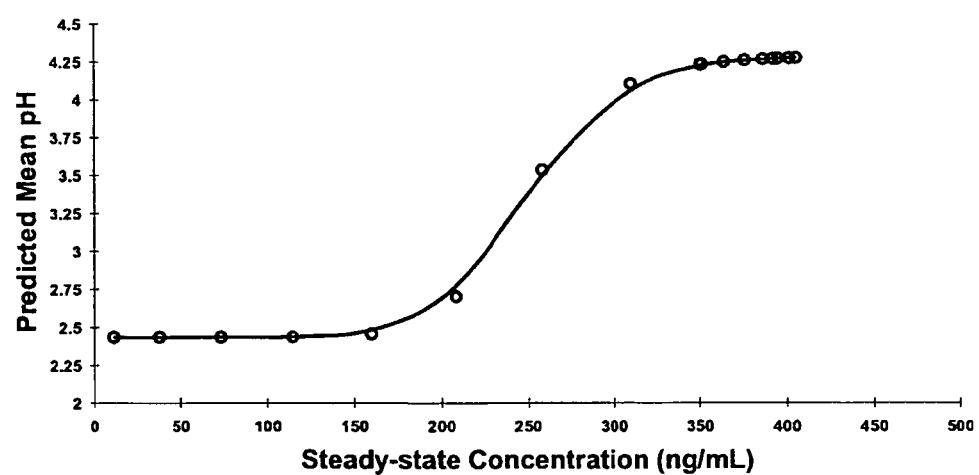

MULTIPLE PPI DOSAGE FORM

CROSS-REFERENCE TO RELATED APPLICATIONS

This application is a continuation of U.S. patent application Ser. No. 11/629,016, filed on Nov. 7, 2008, now U.S. Pat. No. 8,461,187, which is a U.S. national stage entry of International Patent Application No. PCT/US2005/019028, filed on Jun. 1, 2005, which claims priority to U.S. Provisional Patent Application No. 60/580,265, filed on Jun. 16, 2004, the contents of each of which are fully incorporated herein by reference.

TECHNICAL FIELD

The present invention relates to proton pump inhibitors and in particular, relates to dosage forms containing multiple doses of a proton pump inhibitor.

BACKGROUND OF THE INVENTION

Proton pump inhibitors (or "PPIs") are a class of pharmaceutical compounds that inhibit gastric acid secretions by inhibiting H+/K+ adenosine triphosphate, an enzyme present in parietal cells found in the gastric lining of the stomach. H+/K+ adenosine triphosphate is variously referred to as an "acid pump" or "proton pump" and examples of PPI's include lansoprazole, omeprazole, and pantoprazole. PPIs rapidly degrade in acidic environments and therefore, dosage forms containing PPIs generally are designed to protect the PPI from the acidic environment of the stomach. Specifically, such dosage forms are designed such that a single dose of the PPI is released in the upper small intestine where the PPI can be absorbed.

Peak plasma concentrations for PPIs typically occur within 1-3 hours after ingestion, and the half-life of such drugs is generally short, usually less than 2 hours. Notwithstanding the relatively quick peak plasma levels and half-lives associated with PPIs, a prolonged therapeutic effect is attained regardless of their relatively short pharmacokinetic half life. In fact, the therapeutic effect of PPIs does not directly correlate with serum concentrations of these drugs. Accordingly, patients on PPI therapy are generally only required to take a single dosage form containing a daily dose of a PPI, usually prior to breakfast. Unfortunately, although the therapeutic effect of these drugs is longer than would otherwise be anticipated, some patients on PPI therapy experience a nocturnal break through event where the secretory activity of the proton pumps return. As a result, the acidity in the stomach increases and the discomfort associated with the increased acid returns.

Unfortunately, it currently does not appear that there is a solution to the nocturnal breakthrough phenomenon associated with PPIs. There is therefore a need for a dosage form containing a PPI that reliably can provide a full day of therapeutic effect while being administered on a once a day basis.

SUMMARY OF THE INVENTION

The present invention provides dosage forms comprising a PPI that is released from the dosage form as a first and a second dose. Each dose of PPI is present in an amount sufficient to raise the plasma levels of the PPI to at least 100 ng/ml. The PPI may be released from the dosage form as discreet pulses of the drug that are separated by a pre-selected period of time. Alternatively, the first and second doses may be separated by little or no time delay, and therefore provide a continuous release of the PPI over a pre-selected time period. The invention also provides methods of treating gastrointestinal disorders with the dosage forms mentioned above.

DESCRIPTION OF THE DRAWINGS

FIG. 1 is a graph derived from the modeling technique employed in example 1.

DETAILED DESCRIPTION OF THE INVENTION

Notwithstanding attempts to mitigate the so-called nocturnal breakthrough events associated with current PPI dosage forms and regimens, there is still no means for successfully helping the significant population of patients that experience this unpleasant phenomenon commonly associated with PPI therapy. It has unexpectedly and surprisingly been discovered that the breakthrough phenomenon can be mitigated through appropriate use of pharmacokinetic properties of these drugs to establish effective concentrations of the PPI. In particular, it has been found that it is not sufficient merely to provide an additional dose of a PPI sometime after a first daily dose and before nighttime. The appropriate means for alleviating the breakthrough phenomenon is a function of the concentration of the PPI in a patient. Applicants have discovered that there is a threshold concentration of these drugs that must be surpassed in a second dose of the PPI before a therapeutic effect is achieved. Moreover, the first and the second dose can be administered in a single oral dosage form that can be taken once a day to alleviate nocturnal breakthrough events.

Hence, the present invention provides a dosing regimen and dosage form comprising a first dose of a PPI and a second dose of a PPI such that each dose of the PPI is in an amount sufficient to achieve a therapeutic effect and thereby alleviate the nocturnal breakthrough phenomenon. Any PPI is suitable for use in the present invention and examples of PPI's include but are not limited to omeprazole (disclosed in U.S. Pat. No. 4,508,905, herein incorporated by reference), lansoprazole (disclosed in U.S. Pat. No. 4,628,098, herein incorporated by reference), pantoprazole (disclosed in U.S. Pat. No. 4,758, 579, herein incorporated by reference), tenatoprazole (disclosed in U.S. Pat. No. 4,808,596, herein incorporated by reference), and iloprazole (disclosed in U.S. Pat. No. 5,703, 097, herein incorporated by reference), as well as any salts or enantiomers of the foregoing.

The threshold amount of the PPI in either the first or second dose should raise the plasma levels of the PPI to at least 100 ng/ml. Preferably, the amount of drug in the first and second dose is sufficient to raise the plasma concentration above 200 ng/ml, more preferably above 300 ng/ml, even more preferably above 400 ng/ml, and most preferably above 500 ng/ml. Based upon the published clinical literature and skill in the art, those skilled in the art can readily determine the milligram amounts of any particular PPI that should be included in the first and second dose of the PPI to raise patient plasma levels to the thresholds mentioned above.

The benefits of this invention are not limited to a particular type of dosage form having a specific mechanism of drug release. The enhanced efficacy in alleviating nocturnal breakthrough events can be obtained with any dosage form suitable for releasing a PPI such that, for example, a modified release of the drug meets the threshold criteria mentioned above. In view of the discovery of the threshold level, the method of delivery of the PPI is a matter of choice for those skilled in the art.

As a general matter, however, there are two types of modified drug release. Specifically, there is controlled or extended release, and pulsed release. There are three types of formulations commonly used as controlled release dosage forms which include, matrix systems, osmotic pumps, and membrane controlled systems (also referred to as reservoir systems). Each of these systems is described in greater detail below. A detailed discussion of such dosage forms may also be found in: (i) Handbook of pharmaceutical controlled release technology, ed. D. L. Wise, Marcel Dekker, Inc. New York, N.Y. (2000), and (ii) and Treatise on controlled drug delivery, fundamentals, optimization, and applications, ed. A. Kydonieus, Marcel Dekker, Inc. New York, N.Y. (1992).

Matrix systems are well known in the art. In a matrix system, the drug is homogenously dispersed in a polymer and optionally conventional excipients. This so-called admixture is typically compressed under pressure to produce a tablet. Drug is released from this tablet by diffusion and erosion. Matrix systems typically employ a pharmaceutically acceptable polymer such as a water-soluble hydrophilic polymer, or a water insoluble hydrophobic polymer (including waxes). Examples of suitable water soluble polymers include polyvinylpyrrolidine, hydroxypropylcellulose, hydroxypropylmethyl cellulose, methyl cellulose, vinyl acetate copolymers, polysaccharides (such as alignate, xanthum gum, etc.), polyethylene oxide, methacrylic acid copolymers, maleic anhydride/methyl vinyl ether copolymers and derivatives and mixtures thereof. Examples of suitable water insoluble polymers include acrylates, cellulose derivatives such ethylcellulose or cellulose acetate, polyethylene, methacrylates, acrylic acid copolymers and high molecular weight polyvinylalcohols. Examples of suitable waxes include fatty acids and glycerides.

The composition of the invention also typically includes pharmaceutically acceptable excipients. As is well known to those skilled in the art, pharmaceutical excipients are routinely incorporated into solid dosage forms. This typically is done to ease the manufacturing process as well as to improve the performance of the dosage form. Common excipients include diluents or bulking agents, lubricants, binders, etc.

Diluents, or fillers, can be added to, for example, increase the mass of an individual dose to a size suitable for tablet compression. Suitable diluents include, for example, powdered sugar, calcium phosphate, calcium sulfate, microcrystalline cellulose, lactose, mannitol, kaolin, sodium chloride, dry starch, and sorbitol.

Lubricants are incorporated into a formulation for a variety of reasons. They reduce friction between the granulation and die wall during compression and ejection. This prevents, for example, the granulate from sticking to the tablet punches, and facilitates its ejection from the tablet punches. Examples of suitable lubricants include talc, stearic acid, vegetable oil, calcium stearate, zinc stearate, and magnesium stearate.

Glidant's can also be incorporated into a formulation, typically for purposes of improving the flow characteristics of the granulation. Examples of suitable glidant's include talc, silicon dioxide, and cornstarch.

Binders also may be incorporated into the formulation. Binders are typically utilized if the manufacture of the dosage form uses a granulation step. Examples of suitable binders include povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Other excipients that may be incorporated into the formulation include preservatives, antioxidants, or any other pharmaceutically acceptable excipient commonly used in the pharmaceutical industry.

The amount of excipients used in the formulation will correspond to that typically used in a matrix system. The total amount of excipients, fillers and extenders, and the like typically will vary from about 10% to about 80% by weight of the dosage form.

The matrix formulations are generally prepared using standard techniques well known in the art. Typically, they are prepared by dry blending the polymer, filler, drug, and other excipients followed by granulating the mixture using an alcohol until proper granulation is obtained. The granulation is done by methods known in the art. The wet granules are dried in a fluid bed dryer, sifted and ground to appropriate size. Lubricating agents are mixed with the dried granulation to obtain the final formulation.

In an osmotic pump system, a tablet core is encased by a semipermeable membrane having at least one orifice. The semipermeable membrane is permeable to water, but impermeable to the drug. When the system is exposed to body fluids, water will penetrate through the semipermeable membrane into the tablet core containing osmotic excipients and the active drug. Osmotic pressure increases within the dosage form and drug is released through the orifice in an attempt to equalize pressure.

In more complex pumps, the tablet core contains multiple internal compartments. For example, the first compartment may contain the drug and the second compartment may contain a polymer, that swells on contact with fluid. After ingestion, this polymer swells into the drug containing compartment at a predetermined rate and forces drug from the dosage form at that rate. Such dosage forms are often used when are zero order release profile is desired.

Osmotic pumps are well known in the art and have been described in the literature. U.S. Pat. No. 4,088,864; 4,200,098; and 5,573,776; all of which are hereby incorporated by reference, describe osmotic pumps and methods for their manufacture. Osmotic pumps containing compounds, such as omeprazole, have been described in U.S. Pat. No. 5,178,867, the Contents of which are hereby incorporated by reference.

As a general guideline, osmotic pumps are typically formed by compressing a tablet of an osmotically active drug (or an osmotically inactive drug in combination with an osmotically active agent or osmagent) and then coating the tablet with a semipermeable membrane which is permeable to an exterior aqueous-based fluid but impermeable to the passage of drug and/or osmagent. One or more delivery orifices may be drilled through the semipermeable membrane wall. Alternatively, orifice(s) through the wall may be formed in situ by incorporating leachable pore forming materials in the wall. In operation, the exterior aqueous based fluid is imbibed through the semipermeable membrane wall and contacts the drug and/or salt to form a solution or suspension of the drug. The drug solution or suspension is then pumped out through the orifice as fresh fluid is imbibed through the semipermeable membrane.

As previously mentioned, osmotic pumps may contain multiple distinct compartments. The first compartment may contain the drug as described above, and the second compartment may contain an expandable driving member consisting of a layer of a swellable hydrophilic polymer, which operates to diminish the volume occupied by the drug, thereby delivering the drug from the device at a controlled rate over an extended period of time. Alternatively, the compartments may contain separate doses of the drug.

Typical materials for the semipermeable membrane include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 50%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020.

The osmotic agent present in the pump, which may be used when the drug itself is not sufficiently osmotically active, are osmotically effective compounds soluble in the fluid that enters the pump, and exhibits an osmotic pressure gradient across the semipermeable wall against the exterior fluid. Osmotically effective osmagents useful for the present purpose include magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, mixtures thereof, and the like. The osmagent is usually present in an excess amount, and it can be in any physical form, such as particle, powder, granule, and the like. The osmotic pressure in atmospheres of the osmagents suitable for the invention will be greater than zero and generally up to about 500 atm, or higher.

The expandable driving member typically is a swellable, hydrophilic polymer which interacts with water and aqueous biological fluids and swells or expands to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be noncross-linked or cross-linked. The swellable, hydrophilic polymers are in one presently preferred embodiment lightly cross-linked, such cross-links being formed by covalent ionic bonds or hydrogen bonds. The polymers can be of plant, animal or synthetic origin. Hydrophilic polymers suitable for the present purpose include poly (hydroxy alkyl methacrylate) having a molecular weight of from 30,000 to 5,000,000; kappa carrageenan, polyvinylpyrrolidone having molecular weight of from 10,000 to 360,000; anionic and cationic hydrogels;

polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose; cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams, and the like.

The expression "orifice" as used herein comprises means and methods suitable for releasing the drug from an osmotic system. The expression includes one or more apertures or orifices which have been bored through the semipermeable membrane by mechanical procedures. Alternatively it may be formed by incorporating an erodible element, such as a gelatin plug, in the semipermeable membrane. In cases where the semipermeable membrane is sufficiently permeable to the passage of drug, the pores in the membrane may be sufficient to release the PPI in amounts sufficient to meet the plasma threshold. In such cases, the expression "passageway" refers to the pores within the membrane wall even though no bore or other orifice has been drilled there through. A detailed description of osmotic passageways and the maximum and minimum dimensions for a passageway are disclosed in U.S. Pat. Nos. 3,845,770 and 3,916,899, the disclosures of which are incorporated herein by reference.

The osmotic pumps of this invention are manufactured by standard techniques. For example, in one embodiment, the drug and other ingredients that may be housed in one area of the compartment adjacent to the passageway, are pressed into a solid possessing dimension that corresponds to the internal dimensions of the area of the compartment the agent will occupy, or the agent and other ingredients and a solvent are mixed into a solid or semisolid form by conventional methods such as ballmilling, calendaring, stirring or rolhnilling, and then pressed into a preselected shape. Next, a layer of a hydrophilic polymer is placed in contact with the layer of agent in a like manner, and the two layers surrounded with a semipermeable wall. The layering of agent formulation and hydrophilic polymer can be fabricated by conventional two-layer press techniques. The wall can be applied by molding, spraying or dipping the pressed shapes into a wall forming material. Another and presently preferred technique that can be use for applying the wall is the air suspension procedure. This procedure consists of suspending and tumbling the pressed agent and dry hydrophilic polymer in a current of air and a wall forming composition until the wall is applied to the agent-hydrophilic polymer composite. The air suspension procedure is described in U.S. Pat. No. 2,799,241; J. Am. Pharm. Assoc., Vol. 48, pp. 451-459, (1979). Other standard manufacturing procedures are described in Modern Plastics Encyclopedia, Vol. 46, pp. 62-70 (1969); and in Pharmaceutical Sciences, by Remington, Fourteenth Edition, pp. 1626-1678 (1970), published by Mack Publishing Company, Easton, Pa.

Reservoir systems also are well known in the art. This technology is also commonly referred to as microencapsulation, bead technology, or coated tablets. Small particles of the drug are encapsulated with pharmaceutically acceptable polymer. This polymer, and its relative quantity, offers a predetermined resistance to drug diffusion from the reservoir to the gastrointestinal tract. Thus drug is gradually released from the beads into the gastrointestinal tract and provides the desired sustained release of the compound.

These dosage forms are well known in the art. U.S. Pat. Nos. 5,286,497 and 5,737,320, both of which are hereby incorporated by reference, describe such formulations and their methods of production. U.S. Pat. Nos. 5,354,556, 4,952,402, and 4,940,588, all of which are hereby incorporated by reference, specifically discuss using such technology to produce sustained release dosage forms. As further guidance, however, a pellet is formed with a core of a drug, optionally in association with conventional excipeints. This core is then coated with one, or more, pharmaceutically acceptable polymers. Often, the coating polymer is an admixture of a major proportion of a pharmaceutically acceptable water insoluble polymer and a minor proportion of a pharmaceutically acceptable water soluble polymer.

The central core may be prepared by a number of techniques known in the art. Typically the drug is bound to an inert carrier with a conventional binding agent. The inert carrier is typically a starch or sugar sphere. Before the drug is bound to the inert carrier, it is typically blended with conventional excipients to expedite its handling and to improve the properties of the final dosage form. These excipients are identical to those described above for the matrix systems. The quantity of these excipients can vary widely, but will be used in conventional amounts. The central core is then produced by utilizing a binding agent to attach the powdered drug blend to the solid carrier. This can be accomplished by means known in the art for producing pharmaceutical beads. Suitable means include utilization of a conventional coating pan, an automatic coating machine, or a rotogranulator. The production of these central cores is described in more detail in Pharmaceutical Pelletization Technology, ed. I. Ghebre-Sellassie, Marcel Dekker, Inc. New York, N.Y. (1989).

The second major component of a reservoir system is the polymeric coating. As noted above, the polymeric coating is responsible for giving the beads their release characteristics. The polymeric coating may be applied to the central core using methods and techniques known in the art. Examples of suitable coating devices include fluid bed coaters and pan coaters. The application techniques are described in more detail in: i) Aqueous polymeric coatings for pharmaceutical dosage forms, ed. J. W. McGinity, Marcel Dekker, Inc. New York, N.Y. (1997); and ii) Pharmaceutical Dosage Forms: Tablets Vol. 3. ed. H. A. Lieberman, L. Lachman and J. B. Schwartz, Marcel Dekker, Inc. New York, N.Y. pp. 77-287, (1990.

Examples of suitable polymers include ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane or mixtures thereof.

Once the beads have been prepared, they may be filled into capsules as is known in the art. Alternately, they may be pressed into tablets using techniques conventional in the art.

Pulsed release systems, the other broad category of modified release dosage forms, are also well known in the art. Pulsed release systems generally involve a first drug release and a second drug release separated by a predetermined period of time or site of release. Pulsed release systems also may include a combination of immediate release and extended release. Multiple formulation configurations are suitable for pulsed release dosage forms.

For example, osmotic pumps also are suitable for purposes of pulsatile drug release and have been described in U.S. Pat. Nos. 5,017,381 and 5,011,692, both of which are herein incorporated by reference. Generally, the osmotic pump containing the drug is formed and then overcoated with a layer of a drug to provide for two releases of the drug, one from the coating layer and another from the osmotic pump.

Particle or granule systems have also been proposed for purposes of providing a pulsed release of drug. U.S. Pat. No. 6,228,398 (incorporated herein by reference) teach the use of such systems for a pulsed release of a drug. Such systems typically use distinct populations of drug containing particles to achieve a pulsed release. The populations employ different coating polymers, such as those mentioned above, to release the drug at different points in time or location. For example, polymers having different dissolution pHs are commonly used for this purpose. Hence, one population of granules can be coated with a polymer that begins dissolving at a pH of 6 and another population of granules can be coated with a polymer that begins dissolving at a pH of 6.5 to achieve a pulsed release. In this manner, the first population of granules would release the drug in the upper small intestine while the second population of the granules would release the drug further down stream and therefore at a later time.

It will be understood, of course, that any of the dosage forms used in accordance with the present invention may employ an enteric coating or buffering systems such as those described in U.S. Pat. Nos. 6,849,346; 5,026,560; 5,045,321; 4,786,505; and 6,849,346 (all of which are herein incorporated by reference) for purposes of protecting the PPI.

The compositions of the invention can be administered orally in the form of tablets, pills, or the granulate may be loose filled into capsules. The tablets can be prepared by techniques known in the art and contain a therapeutically effective amounts of the PPI compound and such excipients as are necessary to form the tablet by such techniques. Tablets and pills can additionally be prepared with enteric coatings and buffering systems such as those described above to protect the PPI. The coating may be colored with a pharmaceutically accepted dye. The amount of dye and other excipients in the coating liquid may vary and will not impact the performance of the extended release tablets. The coating liquid generally comprises film forming polymers such as hydroxypropyl cellulose, hydroxypropylmethyl cellulose, cellulose esters or ethers (such as cellulose acetate or ethylcellulose), an acrylic polymer or a mixture of polymers. The coating solution is generally an aqueous solution or an organic solvent further comprising propylene glycol, sorbitan monoleate, sorbic acid, fillers such as titanium dioxide, a pharmaceutically acceptable dye.

One skilled in the art, taking into account above teachings will readily be able to formulate oral dosage forms containing a PPI that is released in accordance with the threshold concentrations, also taught above. Thus, for example, when a controlled or extended release formulation is employed, the drug should be released such that the plasma concentration threshold is met during the period the drug is released. Hence, when a extended release formulation is employed according to the present invention, there is a continuous release of the first and second dose of the PPI, and preferably, the plasma level of PPI is maintained above the threshold level during at least part of the combined release of the first and second dose of PPI. Alternatively, when a pulsed release dosage form is employed, the first and second pulses of the drug independently should be sufficient to increase the plasma level concentration above the threshold level.

The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, and rate of excretion of the specific compound employed; the duration of the treatment; drugs used in combination or coincidental with the specific compound employed; and other factors known to those of ordinary skill in the medical arts. For example, it is well within the skill of the art to start doses of the compound at levels lower than required to achieve the desired therapeutic effect and to gradually increase the dosage until the desired effect is achieved.

Formulations of the invention are administered and dosed in accordance with sound medical practice, taking into account the clinical condition of the individual patient, the site and method of administration, scheduling of administration, and other factors known to medical practitioners. As further guidance, however, in cases where a pulsed release dosage form is employed, drug loading for each pulse is independently and typically between 5 mg and 300 mg, more typically between 20 mg and 200 mg. In cases where an extended release dosage form is employed, typical drug loading for the combined first and second PPI dose in such a formulation will be in the range of 50 mg to 1000 mg, and more typically 75 mg to 500 mg.

It has also been discovered, that due to the decreasing absorption in the downstream portions of the gastrointestinal tract, it is preferred to load the dosage forms with the PPI such that the second dose is higher than the first dose of the PPI. Hence, in a pulsed release dosage form the second dose is at least 10% more than the first dose, more preferably, the second dose is at least 50% more than the first dose, even more preferably, the second dose is at least 100% to 200% more than the first dose, and most preferably the second dose is at least 200% to 900% more than the first dose. In continuous release dosage forms of the present invention, the increased second dose is reflected in the total drug loading ranges mentioned above.

In cases where the PPI is delivered in pulses, the period between when the first dose begins to be release and when the second dose begins to be released can be separated by varying amounts of time. Preferably, the onset of release of the doses are separated by between 2 hours and 20 hours, more preferably between 3 hours and 16 hours and most preferably between 4 hours and 12 hours. Of course, any of the pulses released from such a dosage form should achieve the threshold concentration and maintain plasma concentrations above such threshold for at least 30 minutes, preferably one hour to 2 hours, and more preferably between 2 hours to 8 hours. In cases where there is no time separating the pulses, or when the release of the PPI is delivered in an extended or continuous form, the time period for release is also variable but preferably the release is provided over the course of 4 hours to 8 hours, more preferably 3 hours to 12 hours and most preferably 2 hours to 20 hours. Additionally, during this release it is preferable to hold the plasma concentration above a threshold level for at least 4 hours, more preferably at least 6 hours, even more preferably at least 8 hours and most preferably for at least 12 hours.

"Therapeutically effective amounts or dose levels" for purposes herein thus can readily be determined by such considerations as are known in the art. The amount should be effective to achieve improvement, including but not limited to, raising of gastric pH, reduced gastrointestinal bleeding, reduction in the need for blood transfusions, improved survival rate, more rapid recovery, and/or improvement/elimination of symptoms and other indicators as are selected as appropriate measures by those skilled in the art.

"Pharmaceutically acceptable" as used herein includes moieties or compounds that are, within the scope of sound medical judgment, suitable for use in contact with the tissues of humans and lower animals without undue toxicity, irritation, allergic response, and the like, and are commensurate with a reasonable benefit/risk ratio.

It will be understood, of course, that dosage forms formulated according to the present invention can be tested empirically in animal and/or human models to determine the appropriate pK parameters resulting from a given formulation.

The formulation can be administered to those patients who are in need of PPI therapy such as those experiencing any of the maladies that PPIs are indicted for use. For example, patients experiencing gastrointestinal disorders such as acid reflux disease, gastro-esophogeal reflux disease, peptic or duedonal ulcers, Zollinger Ellison Syndrome can be treated to alleviate such disorders by administering the formulation of the present invention to such patients. Advantageously, the dosage form provided herein diminishes the likelihood of nocturnal breakthrough events and therefore also provides a method for mitigating nocturnal breakthrough events.

The following examples are provided to further illustrate the present invention and not intended to limit the invention.

EXAMPLES

Example 1

Threshold Level Modeling

Plasma concentration data obtained following administration of single intravenous doses of lansoprazole in humans was modeled to establish threshold concentrations above which a PPI is effective. Initially, gastric pH measured over the five hours post dosing (under fasting conditions) was plotted as a function of plasma concentration. However, no direct relationship between the gastric pH and the drug's plasma concentration could be established. In effect, plotting the data using these parameters resulted in a counter clockwise loop. An effect compartment model was then used in an attempt to delineate a useful relationship between drug concentration and effect. Accordingly, a model was proposed where a PK compartment was linked to a separate effect compartment. This model proved successful in delineating a trend between intragastric pH and concentration using a small effect compartment linked to the PK compartment. Using the same intravenous data, the pharmacological effect was modeled using sigmoid Emax model and PK was modeled using the two compartment model. The modeling first established the pharmacokinetic characteristics of lansoprazole, then the relationship between drug plasma concentration and intragastric pH was established, and pharacodynamic parameter estimates were obtained. The modeling provided the graph shown in FIG. 1 where the effect compartment concentration (assumed to be the same as the plasma concentration at steady-state) is on the x-axis and gastric pH on the y-axis. As shown by the graphic representation of the modeling, the effect of the drug (rise above baseline) begins at concentrations above, approximately, 100 ng/ml and levels off at concentrations above, approximately, 450 ng/ml. Hence, it was determined that the threshold concentration of approximately 100 ng/ml should be attained for purposes of attaining a minimum change in the desired pharmacological effect from baseline.

Example 2

Site of Absorption Study

This was a Phase 1, open-label, non-randomized, four-period, single-dose, crossover study in 8 healthy adult males.

An extemporaneous formulation containing crushed lansoprazole granules from lansoprazole delayed-release capsules (30 mg) mixed with sodium bicarbonate, starch and a radioactive marker were administered to the study subjects via a remote control capsule. This remote control capsule was comprised of a non-digestible shell capable of holding a drug powder, a release mechanism, and a magnetic receiver that receives an external signal. Upon receiving a remote signal during Periods 1, 2, and 3, the capsule released it's contents in the pre-designated site within the GI tract (see table 1 below). A lansoprazole delayed-release 30 mg capsule with starch and a radioactive marker were administered orally during Period 4 and were used as a bioavailability reference.

Indium-111 chloride ($^{111}$In-chloride) was used as the radioactive marker in the test formulation that was filled into remote control capsule. Each subject also received a second radioisotope, technetium-99m DTPA ($^{99m}$Tc-DTPA), in the water used to swallow the InteliSite Companion capsule. Since the radioisotopes are not absorbed, progress of the formulation through the GI tract was monitored using a gamma camera that captures images at frequent intervals after ingestion of the dose. The radioisotope in the water outlined or "mapped" the GI tract to delineate the targeted site of drug release. Each subject received a single oral dose during each dosing period (fixed sequence) as shown in the table 1 below.

TABLE 1

| Period | Location | Formulation |
|--------|----------|-------------|
| 1 | Cecum/colon | Lansoprazole (30 mg) powder blended with sodium bicarbonate (90.0 mg) in reomote control capsule |
| 2 | Distal small intestine | Lansoprazole (30 mg) powder blended with sodium bicarbonate (90.0 mg) in remote control capsule |
| 3 | Proximal small intestine | Lansoprazole (30 mg) powder blended with sodium bicarbonate (90.0 mg) in remote control capsule |
| 4 | Reference (Stomach) | Lansoprazole (30 mg) delayed release capsule |

The study consisted of 4 dosing periods with a 7-day minimum washout interval between capsule administration in each period. All subjects were confined for up to 3 days in each period; confinement continued 24 hours after the drug was released from the remote control capsule. Serial blood samples were taken following drug release to determine segmental absorption and pharmacokinetics of lansoprazole.

Blood samples were obtained on Study Day 1 of each period prior to dosing and just before the investigational product was released from remote control capsule (0 Hour) and at 0.25, 0.5, 0.75, 1, 1.5, 2, 4, 6, 8, 12, 16 and 24 hours after release of lansoprazole in the selected segment of the GI tract. Blood samples for evaluation of lansoprazole pharmacokinetics following administration of lansoprazole 30 mg delayed release capsule were collected at the same timepoints as the remote control capsule. Timing for the pharmacokinetic samples were relative to time of release in the GI tract for the remote control capsule doses or relative to time of administration for the delayed release capsule.

The relative bioavailability of lansoprazole delivered to the proximal small intestine, distal small intestine, or colon compared to the delayed release lansoprazole capsule was calculated as the ratios of $AUC_\infty$ for different GI regions to that of the delayed release capsule. In addition, the relative bioavailability of lansoprazole delivered to the distal small intestine and colon compared to the proximal small intestine was calculated.

The rate and extent of absorption for lansoprazole from the distal small intestine were less than those obtained for the proximal intestine, although the absorptions were comparable. The extent of absorption was reduced when lansoprazole was directly delivered to the colon, the relative bioavailability of lansoprazole from the colon compared to the lansoprazole delayed release capsule was between approximately 10% to 60%.

While the invention has been described in detail and with reference to specific embodiments, it will be apparent to one skilled in the art that various changes and modifications may be made to such embodiments without departing from the spirit and scope of the invention.

What is claimed is:

1. A dosage form comprising a PPI wherein the PPI is released from the dosage form as a first and a second dose, wherein the first and second doses are released from the dosage form as discreet pulses of the PPI separated by a period of time, wherein the second dose contains at least 10% more of the PPI than the first dose, and wherein each of the first and second doses comprise a sufficient amount of the PPI to raise plasma levels of the PPI to a threshold concentration of at least 100 ng/ml, wherein the PPI is lansoprazole or any salts or enantiomers thereof.

2. The dosage form of claim 1, wherein the PPI is lansoprazole or enantiomers thereof.

3. The dosage form of claim 2, wherein the PPI is lansoprazole.

4. The dosage form of claim 2, wherein the second dose begins to be released between 2 and 20 hours after the first dose begins to be released.

5. The dosage form of claim 2, wherein the second dose begins to be released between 3 hours and 16 hours after the first dose begins to be released.

6. The dosage form of claim 2, wherein the second dose begins to be released between 4 hours and 12 hours after the first dose begins to be released.

7. The dosage form of claim 2, wherein each pulse of the PPI is sufficient to maintain plasma concentrations above the threshold concentration for at least 30 minutes.

8. The dosage form of claim 2, wherein the second dose contains at least 50% more than the first does.

9. The dosage form of claim 2, wherein the second dose contains at least 100% to 200% more than the first dose.

10. The dosage form of claim 2, wherein the second dose contains at least 200% to 900% more than the first dose.

11. The dosage form of claim 2, wherein the first and second doses independently comprise between 5 mg and 300 mg of the PPI.

12. The dosage form of claim 2, wherein the first and second doses independently comprise between 20 mg and 200 mg of the PPI.

13. The dosage form of claim 2, wherein each of the first and second doses comprise a sufficient amount of the PPI to raise plasma levels of the PPI to a threshold concentration of at least 200 ng/ml.

14. The dosage form of claim 2, wherein each of the first and second doses comprise a sufficient amount of the PPI to raise plasma levels of the PPI to a threshold concentration of at least 300 ng/ml.

15. The dosage form of claim 2, wherein each of the first and second doses comprise a sufficient amount of the PPI to raise plasma levels of the PPI to a threshold concentration of at least 400 ng/ml.

16. The dosage form of claim 2, wherein each of the first and second doses comprise a sufficient amount of the PPI to raise plasma levels of the PPI to a threshold concentration of at least 500 ng/ml.

17. The dosage form of claim 2, wherein the period of time is between 2 hours and 20 hours.

18. The dosage form of claim 2, wherein the period of time is between 3 hours and 16 hours.

19. The dosage form of claim 2, wherein the period of time is between 4 hours and 12 hours.

20. The dosage form of claim 2, wherein the dosage form is a matrix system.

21. The dosage form of claim 2, wherein the dosage form is a reservoir system.

22. The dosage form of claim 2, wherein each dose is in an amount sufficient to achieve a therapeutic effect and thereby alleviate nocturnal breakthrough phenomenon.

* * * * *